(12) United States Patent
Van Brunt

(10) Patent No.: US 9,237,982 B2
(45) Date of Patent: Jan. 19, 2016

(54) HIGH FREQUENCY CHEST WALL OSCILLATION APPARATUS

(71) Applicant: Nicholas P. Van Brunt, White Bear Lake, MN (US)

(72) Inventor: Nicholas P. Van Brunt, White Bear Lake, MN (US)

( * ) Notice: Subject to any disclaimer, the term of this patent is extended or adjusted under 35 U.S.C. 154(b) by 435 days.

(21) Appl. No.: 13/798,955

(22) Filed: Mar. 13, 2013

(65) Prior Publication Data

US 2013/0267877 A1 Oct. 10, 2013

Related U.S. Application Data

(60) Provisional application No. 61/620,675, filed on Apr. 5, 2012.

(51) Int. Cl.
| | |
|---|---|
| A61H 7/00 | (2006.01) |
| A61H 19/00 | (2006.01) |
| A61H 9/00 | (2006.01) |
| A61H 23/04 | (2006.01) |
| A61M 16/00 | (2006.01) |

(52) U.S. Cl.
CPC ............ *A61H 9/0007* (2013.01); *A61H 9/0078* (2013.01); *A61H 23/04* (2013.01); *A61H 2201/1215* (2013.01); *A61H 2201/165* (2013.01); *A61H 2201/1621* (2013.01); *A61H 2201/5005* (2013.01); *A61H 2201/5071* (2013.01); *A61H 2230/06* (2013.01); *A61H 2230/40* (2013.01); *A61M 16/0006* (2014.02)

(58) Field of Classification Search
CPC ..... A61H 9/0007; A61H 9/0078; A61H 9/00; A61H 9/005; A61H 9/0092
See application file for complete search history.

(56) References Cited

U.S. PATENT DOCUMENTS

| | | | |
|---|---|---|---|
| 6,036,662 A | 3/2000 | Van Brunt et al. | |
| 6,254,556 B1 | 7/2001 | Hansen et al. | |
| 6,736,785 B1* | 5/2004 | Van Brunt | A61H 31/00 |
| | | | 601/44 |
| 6,916,298 B2 | 7/2005 | Van Brunt et al. | |
| 7,115,104 B2 | 10/2006 | Van Brunt et al. | |
| 7,762,967 B2 | 7/2010 | Warwick et al. | |
| 7,785,280 B2 | 8/2010 | Kivisto | |
| 2002/0111571 A1 | 8/2002 | Warwick et al. | |
| 2008/0294075 A1* | 11/2008 | Nozzarella | A61H 9/0078 |
| | | | 601/44 |
| 2009/0192421 A1 | 7/2009 | Huster et al. | |
| 2010/0256540 A1* | 10/2010 | Yamashiro | A61H 9/0078 |
| | | | 601/44 |
| 2012/0016282 A1 | 1/2012 | Van Brunt et al. | |
| 2012/0065561 A1* | 3/2012 | Ballas | A61H 9/0021 |
| | | | 601/152 |

FOREIGN PATENT DOCUMENTS

WO 02053083 A2 7/2002

OTHER PUBLICATIONS

The International Search Report mailed Jun. 27, 2013 for International Application No. PCT/US2013/030869.
The European Search Report mailed Oct. 26, 2015 for European Application No. 13771953.0.

* cited by examiner

*Primary Examiner* — Justine Yu
*Assistant Examiner* — Kathrynn Reilly
(74) *Attorney, Agent, or Firm* — Kinney & Lange, P.A.

(57) ABSTRACT

A high frequency chest wall oscillation (HFCWO) apparatus for the purpose of lung airway clearance of people includes an inflated vest type garment worn around the chest of a person. An oscillating pressure generator with reduced power requirements and a power source is integrated with the garment so that the complete apparatus is wearable by the person. Improvements in pressure waveforms, safety and compliance to prescribed use are disclosed.

17 Claims, 3 Drawing Sheets

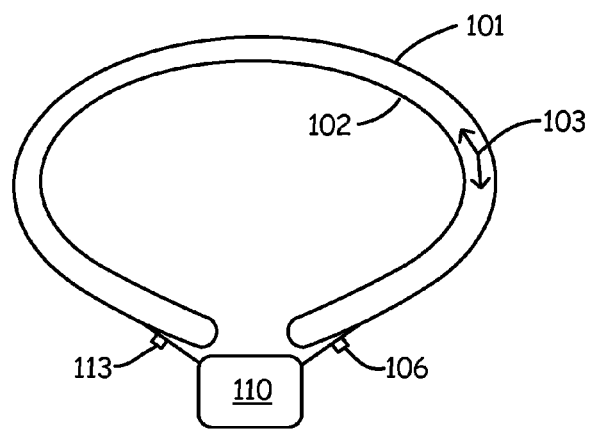
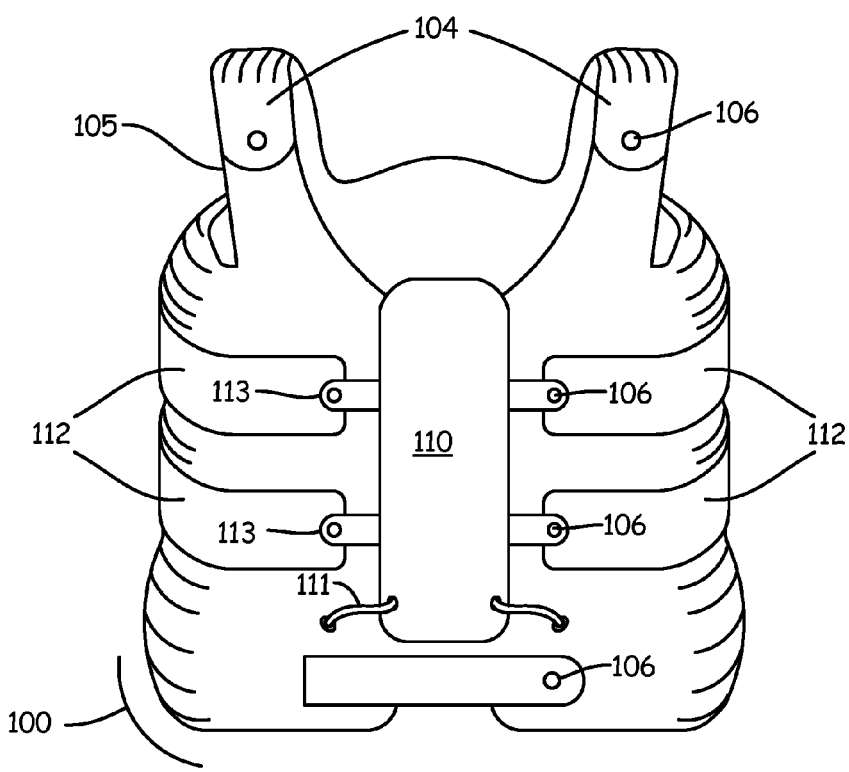

HIGH FREQUENCY CHEST WALL OSCILLATION APPARATUS

CROSS-REFERENCE TO RELATED APPLICATION(S)

This application is a non-provisional of U.S. Provisional Patent Application No. 61/620,675 filed Apr. 5, 2012 entitled "HIGH FREQUENCY CHEST WALL OSCILLATION APPARATUS".

BACKGROUND

The present invention relates to high frequency chest wall oscillator (referred to hereafter as HFCWO) devices.

In a variety of diseases such as cystic fibrosis, emphysema, asthma, and chronic bronchitis, the mucus that collects in the airways is difficult to remove by coughing. This may be due to the viscosity or quantity of the mucus or because the patient does not have the strength or lung capacity to produce an adequate cough. Prior art HFCWO devices have been developed that are commercially available standards of care for airway mucus clearance. They promote airway mucus clearance by generating rapidly oscillating externally powered cough like air flows and pressures in the airways of a patient. U.S. Pat. Nos. 7,762,967, 7,115,104, 6,254,556 and 6,036,662 disclose the designs of some popular devices. These are typically prescribed to be used once or several times per day, in sessions of up to about 30 minutes each.

Popular prior art devices are composed of an air pulse generator connected by pneumatic tubing to a vest like garment with an air bladder worn in contact with and surrounding a person's chest. Air pulses cyclically oscillate to alternately pressurize and depressurize the bladder to apply cyclic pressures to the person's chest. Cycle rates can typically be selected from between about 5 to 25 cycles per second. Many of these devices use an air pulse generator that cycles the bladder pressure between about 0 to 1 PSI. Power consumed by some of these devices at the high frequency settings has been measured to be over 200 watts. We have found that, at cycle rates above about 12 cycles per second, an increasing majority of this power is wasted due to inertial effects of the pressure pulses rapidly reversing directions through the tubes connecting the pressure generator and the vest as well as turbulent flow of the transferred volumes of air throughout the system.

A portable solution was attempted as disclosed in U.S. Pat. No. 6,736,785. This invention included a band wrapped around the chest of a person. The circumference of the band was oscillated by mechanical means to apply oscillating force on the person's chest. Several means for allowing chest movement during inspiration and expiration were also disclosed. This design eliminated the energy losses associated with the high air flows within and between the system components of the popular pneumatic systems which demonstrated significant power reductions. Also the mechanical oscillator was much smaller than the pneumatic oscillators. However, this design was not developed into a fully practical device. The chest band concentrated the pressure on the chest to a much smaller area than that of pneumatic vests disclosed in prior art. Because of this, for an effective amount of energy transfer to the person's chest, it was found that an intolerable level of discomfort resulted which would greatly reduce compliance to a prescribed usage routine. This was most severe at higher oscillation frequencies. With the disclosed chest band design the mechanism that oscillated the band produced chest pressure variations that were constant in amplitude over the range of oscillation frequencies. With this, as the frequency increased, the energy transfer to the chest increased proportionately. Allowing a 4:1 ratio of high to low frequency, the energy transfer became excessive and intolerable at high frequencies. Many of the other prior art devices use a constant displacement type pump or reciprocating diaphragms to generate the pressure pulses so, in theory, these would be expected to present the same problem of excessive energy to the persons chest at high frequencies. Measurements show that they actually do, but to a much lesser extent than theory would predict. This is because the substantial air flow related power losses of the pneumatic systems increase rapidly with increasing frequency and tend to attenuate the pulses delivered to the vest and person's chest at those higher frequencies. U.S. Pat. No. 7,785,280 discloses a means of varying the stroke length of a pneumatic type pressure oscillator that could correct this and provide other benefits. To solve this problem in a portable system something similar to the variable stroke mechanism of U.S. Pat. No. 7,785,280 could, in concept, be included but the added complexity and size of the various linkages and control may be poorly suited to a compact wearable device.

Reliable and failsafe operation of all these devices is important. To be offered commercially for medical treatment of people, an FDA approval based on extensive safety analysis is required. This includes consideration of potential device malfunction and misuse. The potential to transfer injurious forces to the chest of the person due to improper use is possible with some prior art designs, as is the possibility of a device malfunction that prohibits the benefits of using such devices.

Efficacy of new devices is also a requirement for FDA approval. Experience with the application of these types of devices has proven that their efficacy is maximized when they have simple user controls, generate proven effective chest wall oscillation wave shapes, amplitudes and frequencies, and encourage compliance to a prescribed usage routine through optimized comfort, ease of use and vanity issues. The present invention provides improvements that encourage compliance to prescribed usage enhancing the long term efficacy of the device. It also provides improvements in the generation and control of the chest wall oscillation waveform to enhance the efficiency of each airway clearance session.

This disclosure provides a system including an air pulse generator, a power source and a vest that are uniquely small and efficient enough to be integrated into a wearable and transportable portable device for use on an ambulatory patient. Treatment sessions with this would be less intrusive allowing a person to stand and move about at will during the sessions rather than being confined to a support, such as a bed. Also, evidence shows that HFCWO is more effective when the person is standing. It is projected that exercise during treatment sessions could also increase the efficacy of HFCWO.

When the pressure generator and power source are integrated with the vest and worn on the person, additional safety features are needed in the design. Risks not present with a sedentary device arise when all these components are strapped to the person. The disclosed invention is a unique and effective solution that is portable, wearable, comfortable, safe and easy to use having the ability to vary the amplitude of the oscillating air pulses as needed to optimize efficacy as oscillation frequency, patient size and disease conditions vary.

SUMMARY

In one embodiment, a high frequency chest wall oscillator wearable about the chest of a user of the type having an inflatable vest with retractable bands attached thereto has a plurality of sinusoidal pneumatic pressure generators. The output amplitude of each of the plurality of pressure generators is limited to prevent harm to a user. The plurality of sinusoidal pneumatic pressure generators produce an oscillating pressure waveform within the vest.

In another embodiment, a high frequency chest wall oscillator has a garment that covers at least a portion of a torso of a user having an inflatable chamber, a blower for providing pressurized air to the inflatable chamber, a plurality of straps that extend around a portion of the torso, and a pressure generator connected to the plurality of straps. The pressure generator produces an oscillating pneumatic pressure waveform in the garment.

BRIEF DESCRIPTION OF THE DRAWINGS

FIG. 1A is a cross sectional view of an HFCWO apparatus and FIG. 1B is a frontal view of an HFCWO apparatus.

DETAILED DESCRIPTION

Figure 2:
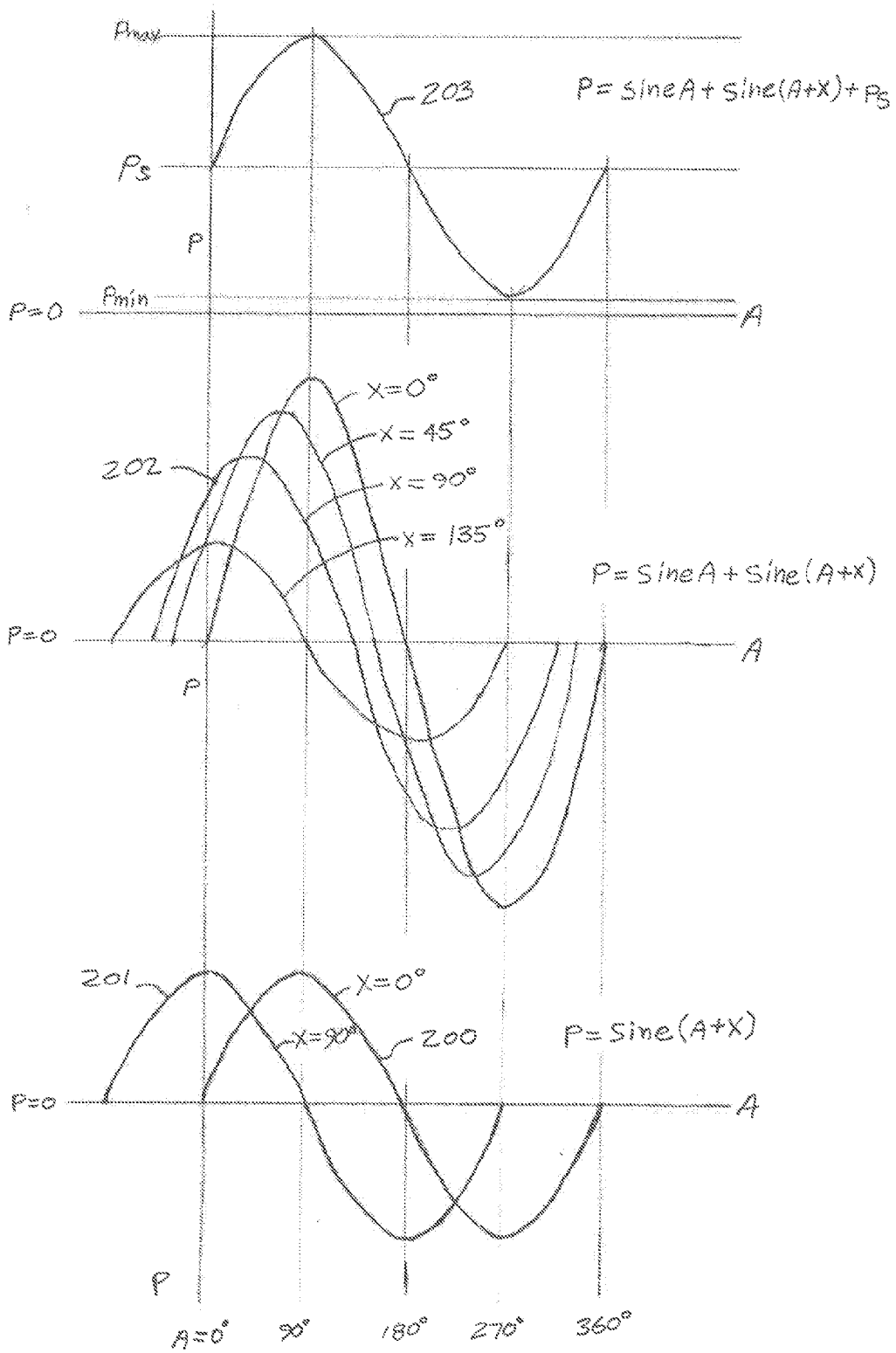
FIG. 2 illustrates pressure waveforms generated during operation of the HFCWO apparatus.

A person wears a vest like garment that continuously surrounds their chest front back and sides from about the shoulders to the waist. The vest has an inner surface in contact with the person's chest joined with an outer surface to contain a volume of pressurized air that exerts force on the inner surface and the person's chest. The confined volume of air between the inner and outer surfaces of the vest is maintained at a selectable pressure range above that of the surrounding atmosphere. The vest structure and material is substantially air tight and flexible. A large contact area with the person's chest reduces pressure concentrations to optimize comfort.

A plurality of high frequency oscillating pressure generators is combined with a constant pressure generator to produce a net pressure waveform with high frequency peaks and valleys that oscillates above atmospheric pressure. The amplitude, wave shape, pressure range and frequency of the pressure waveform within the vest are selectable.

A constant pressure air pump output is connected to the pressurized air volume of the vest. The outer surface of the vest is surrounded circumferentially by a plurality of flexible straps. Each strap includes a motor driven mechanical system that oscillates the circumference of that strap in a substantially sinusoidal pattern. This oscillates the volume of the air in the vest surrounded by the length and width of each strap causing an oscillating pressure change in the entire vest volume. That pressure is spread evenly over the large chest contact area between the vest and the person. Multiple independently oscillated straps allow a large range of selectable control of the oscillating pressure waveform. Two straps oscillated in a sinusoid at the same frequency but with one shifted in phase a selectable amount relative to the other produce pressure oscillations that combine in the vest enclosed volume to produce a sinusoidal pressure pattern of the same frequency but with amplitude that is increased or decreased according to their relative phase shift. The phase shift is electronically controlled by a microcontroller and software through motor drive electronics to produce the desired oscillating pressure amplitude for optimal therapeutic efficacy over the range of frequencies, patient sizes and disease states.

In other operating modes, multiple independent straps each oscillating at differing frequencies and phase angles can allow the generation of non sinusoidal pressure waveforms that could be found to enhance efficacy for some people and conditions. This device can support explorative studies of these alternatives.

Pressure generation systems that have absolute limits of their maximum pressures in the presence of failure modes are included. Energy storage batteries are protected from damaging voltages, currents and temperatures by dedicated systems. Electrical currents and voltages are limited to safe levels during normal operation as well as during failure modes.

FIG. 1A is an external frontal and cross sectional view of the apparatus and FIG. 1B is an external frontal view of the apparatus. This is a vest type of garment 100 worn by a person. It has shoulder straps 104 and arm openings 105 to keep it positioned approximately between the shoulders and waist of a person when it is worn. Connectors 106 can be released to allow the left and right sections to be separated for placement or removal of the vest from the person. The vest has an inner surface 102 and an outer surface 101 that are made from a substantially air tight and flexible material having a minimal tendency to stretch at the intended operating pressures. The inner surface 102 is sized and shaped to fit comfortably and snuggly around the chest of a person while the vest is inflated. A range of vest sizes is provided for a range of chest sizes. The outer surface 101 is larger than and separated from 102 forming a volume of enclosed air 103 between the two surfaces. The volume of air 103 is maintained at a pressure above atmospheric by pressure generator 110 so that outer surface 101 is kept in tension and inner surface 102 is kept compressed against the person's chest. Pressure generator 110 passes pressurized air through pneumatic tubing 111 connected to outer surface 101 and into volume 103. Flexible non stretchable straps 112 surround outer surface 101 and are sized to be slightly smaller in circumference than 101 so that 101 is pressed against straps 112 at the area where they overlap when volume 103 is pressurized. The ends of straps 112 are attached to pressure generator 110 by connectors 106 and 113. Pressure generator 110 moves connections 106 and 113 toward and away from each other in an oscillating sinusoidal pattern. This oscillates the circumference of straps 112 and outer surface of the vest 101 where they overlap which oscillates the size of confined volume 103 thereby generating an oscillating pressure in the entire connected volume of 103.

Each strap 112 circumference is oscillated by pressure generator 110 with independent control of their relative frequency and phase. Two straps are shown in the figure. Physical size limitations of preferred components allow at least three identical independently controlled straps. By combining the sinusoidal pressure oscillations of each strap, the size and shape of a resulting pressure waveform in volume 103 and thereby against the person's chest can be produced with a range of amplitude and shapes including non sinusoidal.

FIG. 2 illustrates pressure waveforms generated with one useful mode of operation. In this mode we use two independently controlled straps oscillating in a sinusoidal pattern with equal amplitudes and frequency but with variable relative phase angle. Curve 200 represents the pressure waveform within volume of air 103 that would result from the sinusoidal oscillation of the circumference of just a single strap 112. It follows the equation P=sine (A+X) where P is pressure, A is angle of the cycle from 0 to 360 degrees and X is a phase shift angle. Using this one strap as the reference we define X=0. A second strap oscillating singly without the first with a relative phase angle of 90 degrees is shown at 201. The two straps oscillating concurrently produce pressure curves that combine in shared volume 103 following the equation P=sine A+sine (A+X). This pressure curve is shown at 202. The other curves on this plot are the result of different values of phase angle X between the two concurrently oscillating straps. Each result is also sinusoidal in shape but reduced in amplitude as the phase angle X is increased. When X=180 degrees the resultant oscillation is zero and when X=0 degrees the amplitude is double that of a single strap. There is a phase angle that produces any desired pressure amplitude from 0 to 2 times a single strap's amplitude.

Curve 203 is a preferred pressure waveform for vest volume 103. On this plot P=0 is where pressure is equal to the surrounding atmosphere commonly referred to as gauge pressures. Pmin is the minimum pressure needed to keep the vest in contact with the person's body and the outer surface from becoming slack. Pmax is the peak pressure before discomfort is likely. These will need to be selected for different oscillation frequencies, patient size and condition and vest size. The difference between Pmax and Pmin is set by the phase angle as described above. Ps is the mid pressure between the oscillating pressure peaks and valleys. This is set by a static pressure source 300 that is connected with volume 103 to combine with the oscillating pressures 202 causing that entire pressure curve to be shifted upward (higher pressure) so that it is always above zero. The resulting final pressure equation for 203 inside the vest in volume 103 becomes P=sine A+sine (A+X)+Ps.

Figure 3:
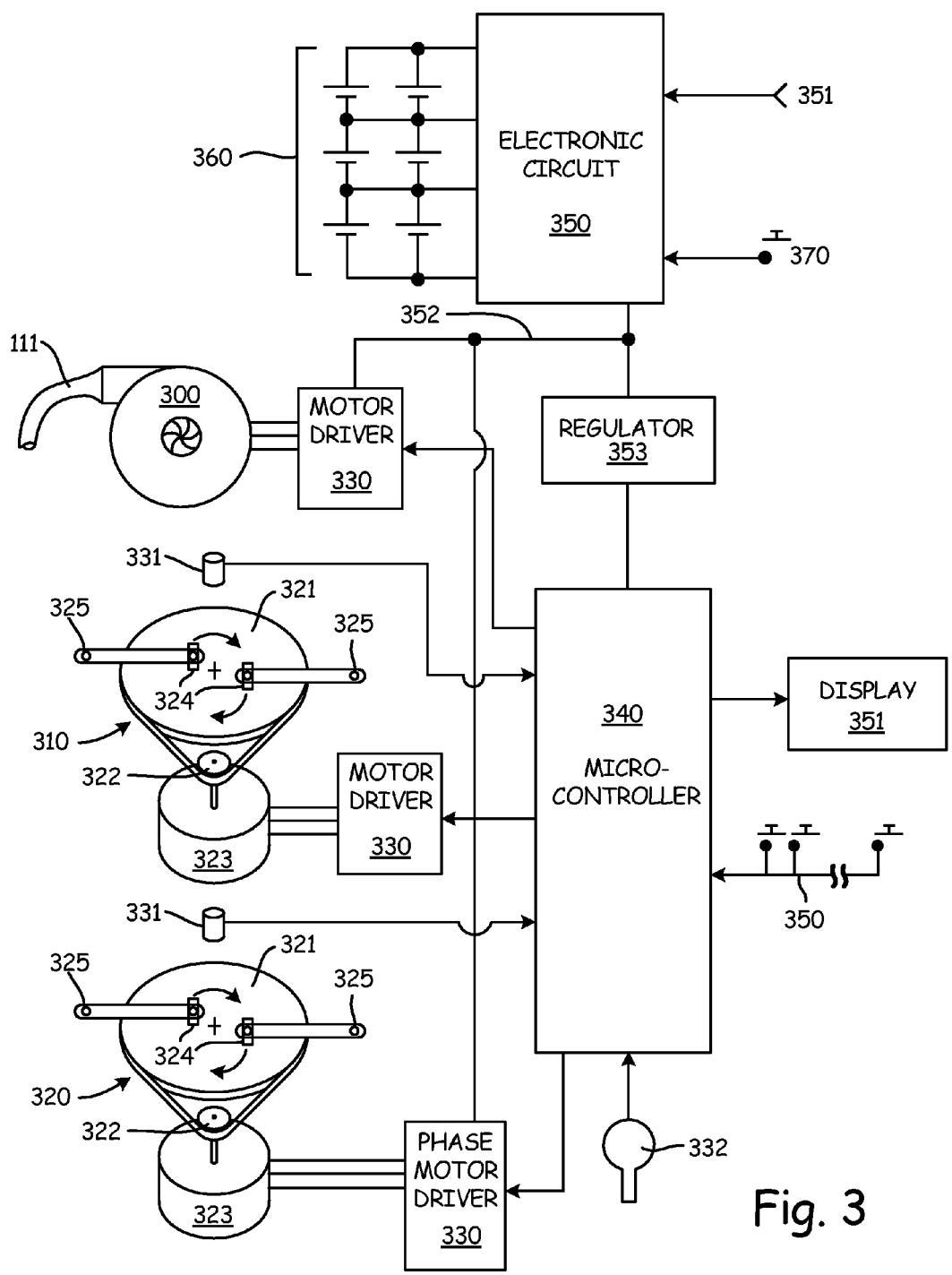
FIG. 3 is a schematic diagram of the major components of a pressure generator for the HFCWO.

FIG. 3 is a schematic diagram of the major components that are included in the pressure generator referenced as 110 in FIG. 1. 300 is a variable speed blower used as the static pressure source. A blower type with an impeller driven by a 3 phase brushless motor is preferred. Blowers commonly used in CPAP devices such as Micronel model #U51DX can have suitable specifications. They allow air to backflow from the vest through the blower when the vest pressure exceeds the blower pressure as the person's chest expands during inhalation. Blower 300 is connected at its output to the vest volume 103 by pneumatic tube 111. The air flow rate between the blower 300 and the vest 103 needs to be high enough to allow easy slow movement of the person's chest during normal tidal breathing but low enough to not allow significant venting of the much higher frequency pressure oscillations. This can be fine tuned if need by choosing the inside diameter of tube 111.

320 is a symbolic grouping of a combination of components that oscillate one of a plurality of straps 112 that wrap around the vest. 321 and 322 are connected gears or sprockets of differing size ratio that may be used to allow the motor 323 to rotate within an efficient speed range of several thousand RPM while driven component 321 rotates at a reduced rate driving the 5 to 25 Hz oscillation rate of the straps 112. Alternately, a thin and larger diameter motor may be found or fabricated that operates at lower RPM with enough torque and efficiency to not require the speed reducer 321 and 322. As 321 rotates, it is connected to crankshaft 324 having two pins offset from its center of rotation equal and opposite amounts. The pins trace 180 degree opposite sides of a circular path of fixed radius causing connected linkages 325 to move alternately toward and away from each other. The other ends of the linkages are connected to the ends of the strap 112 causing the ends of the strap to move alternately toward and away from each other in an approximate sinusoidal oscillation of its circumference. The preferred type of motor 323 is a 3 phase brushless motor with stationary electromagnetic coils in its center and an outer rotating array of permanent magnets and steel housing. These tend to be high torque motors with a high moment of inertia to helps smooth a pulsating torque load such as this. A suitable example would be a Maxon model EC 45 flat motor. Additional oscillators for additional straps are indicated by 310. These blocks have the same details as shown in 320.

All the motors are driven by brushless 3 phase motor drivers 330. These are controlled by digital outputs from microcontroller 340. Relative oscillator phase is sensed by 331 and are input to the microcontroller. Pressure sensor 332 monitors vest pressure in volume 103 and is input to the microprocessor. Desired phase angles, oscillation rates and pressures are all maintained by software control of motor driver signals output from microcontroller 340. Microcontroller software performs commutation of motors 323 giving the software total control of the motors rotational position. Combining this with the position reference signal indicating position of 321 from sensor 331, the oscillation phase of strap 112 can be accurately determined and controlled by the software algorithm. The pressure output of the preferred blower 300 is closely related to the impeller speed driven by its included motor. That motor is also commutated by the software giving it complete control of its speed and therefore its pressure output.

User inputs are supplied to the microprocessor by switches 350 and operational status is displayed to the user by display 351. Information such as remaining time to completion of the current session, reminder of time for next session, remaining battery capacity and abnormal operating conditions can be displayed. A prescribed usage routine for a given person can be coded into the memory of the microcontroller 340. 340 includes a real time clock readable by the software to keep record of actual device usage time and duration. Software running in the microcontroller 340 can compare the prescribed usage to the actual usage and indicate this through display 351. This can be used as an incentive or reminder to the person using the device or their care giver. This can also be useful information for the physician or the researcher performing clinical studies. A person could attempt to avoid use of the device and generate a false record of usage by operating it without attachment to that person. However, pressure sensor 332 can be chosen with a high sensitivity of 0 to 1 PSI total range and, in combination with an included high gain amplifier, both respiratory patterns and heart rates can be detected as pressure changes by software in the microcontroller in a lightly inflated vest. It can be determined from this that the device is or isn't being worn during treatment sessions. If exercise is prescribed during treatment then this can be verified by measurement of an increased heart rate as detected through pressure sensor 332 and decoded by the software.

Power is from battery array 360. A good choice here is lithium ion cell type 18650. 6 of these connected as shown weigh about 300 grams and provide about 60 watt hours of electrical energy. This is enough for one day of prescribed use with recharge each night. These cells have a very high energy density. Usage outside of their specified operating range is to be avoided and must be eliminated when the cells are worn on the person. FDA approval of a device of this design will require proof of this. Electronic circuit 350 is dedicated to storage cell protection. It continuously monitors cell temperature, charge current, charge voltage, discharge current and discharge voltage. Any deviation from these specified safety limits detected by circuit 350 will cause the cells to be immediately disconnected electrically from charging input 351 and output bus 352 by opening electronic switches contained in circuit 350. Blower 300 and pressure oscillators 320 consume most of the power from the cells. Current flows from bus 352 through motor drivers 330 to the motors 323 and 300. A short circuit, locked rotor or any other failure in these paths that could draw excessive power and risk over heating would produce an excess cell discharge current that would immediately disconnect the current path from the cells by the action of circuit 350 before significant heating could occur. The remainder of the electronics is low power circuitry. A short circuit here may not produce a high enough current draw to disconnect the cells but could cause a small local high temperature. All low power current paths (mostly not shown in the figure) could pass through regulator 353. This component limits the current passing through it to a very low level that could not cause any significant heating. The total battery 360 voltage is around 12 volts or less. There are no voltage boost circuits. No shock hazard can exist from this. Low operating voltage in combination with the protection circuits described, eliminate all possible electrically related hazards. Mechanical hazards are limited to those that could generate unsafe pressures on the chest of the person. The oscillating pressure generators 320 oscillate the circumference of straps 112. The amplitude of this oscillation is determined entirely by the diameter of the circle traced by the rotating pins of crankshafts 324. There is no failure mode that can make this circle diameter larger. This, multiplied by the width of straps 112, will determine the volume and pressure change of the vest as discussed. There is also no failure mode that can increase the width of the straps so the oscillating pressure mechanism disclosed is intrinsically safe from failures. The constant pressure blower 300 can potentially cause an unsafe static pressure in the vest. Thus, there is no failure of the blower 300 in isolation that could cause it to produce a pressure in excess of what would be expected from its power inputs. The preferred blower would be driven by a rotating 3 phase voltage sequence of pulses that feed the motor windings. Each voltage pulse is pulse width modulated to control the power delivered to the motor and the blower's maximum rotational speed. This is a common scheme of brushless motor control familiar to anyone skilled in the art. In the disclosed design, the motor drivers 330 would deliver pulses at 100% duty cycle nearly equal in voltage to the maximum battery voltage. This will define a maximum possible motor and rotor speed and therefore a maximum pressure. There is no source of higher voltage or duty cycle that can be fed to the motor due to a failure. So, in the preferred embodiment, a blower should be chosen or designed for this device to produce a maximum pressure at maximum battery voltage and 100% duty cycle drive pulses that is below the safety limit for a person. With this, no blower related unsafe faults can exist.

As an additional final safety feature, a simple emergence power off button 370 is included that disconnects all power from the device immediately when activated.

There is another class of faults that does no immediate harm to the person but is damaging none the less. These are faults that can cause the therapy to become reduced or ineffective without being noticed by the person. Faults such as a leaky vest, a blocked blower inlet or motor failure are several of many potential faults in this category. Most, perhaps all, of these cause an unexpected pressure waveform in the vest. The prescription for use can be stored in the microcontroller memory as discussed. This can include the expected pressure waveforms during treatment sessions for this person with a reasonable variation tolerance. The pressure sensor 332 can capture the actual pressure waveform during each session and compare it to stored expected limits. A pressure waveform failure warning can be displayed on 351 and a record of failure history can be saved in the microcontroller memory for diagnostic evaluation.

Discussion of Possible Embodiments

The following are non-exclusive descriptions of possible embodiments of the present invention.

A HFCWO apparatus produces an oscillating pneumatic pressure waveform by combining the outputs from a plurality of sinusoidal pneumatic pressure generators where each pressure generator's oscillation frequency and oscillation relative phase angle can be independently controlled to set the shape, frequency and amplitude of the resultant combined pressure waveform.

A HFCWO apparatus includes a vest like garment worn around the chest of a person with inner and outer surfaces and a pressurized volume of air between the surfaces with one or more bands surrounding the outer surface of the vest circumference that are cyclically shortened then lengthened to oscillate the volume of the air between the outer and inner surfaces of the vest to generate an oscillating pressure waveform in the vest air volume.

A HFCWO apparatus includes a vest like garment worn around the chest of a person that transfers an oscillating pressure waveform with a frequency range between 5 to 25 HZ and pressure waveform between 0 and 1 PSI to the person's chest while requiring less than 100 watts of electrical power.

A HFCWO apparatus powered by batteries with the entire apparatus and batteries worn around the chest of a person.

A HFCWO apparatus produces an oscillating pneumatic pressure waveform by combining the outputs from a plurality of sinusoidal pneumatic pressure generators where each pressure generator's output amplitude is limited so that there is no possible combination of outputs or apparatus failure mechanisms that can result in a combined waveform that could be harmful to the person receiving the HFCWO.

A HFCWO apparatus worn around the chest of a person having its entire electrical system and battery designed with failsafe shock and fire protection circuitry.

A HFCWO apparatus includes a pneumatic pressure sensor and microcontroller to continuously monitor operating pressure waveforms and warns the person if the pressure waveforms fall outside safe or efficacious limits.

A HFCWO apparatus includes a pneumatic pressure sensor and microcontroller to compare operating pressure waveforms with prescribed settings.

A HFCWO apparatus that monitors and records the time and duration of therapy sessions and determines whether each therapy session was performed on an actual person by detecting a heart rate or breathing cycle.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A high frequency chest wall oscillator comprising:
a garment having an inflatable chamber that covers at least a portion of a torso of a user;
a blower for providing pressurized air to the inflatable chamber;
a plurality of straps that extend around the inflatable chamber of the garment; and
a pressure generator connected to the plurality of straps;
wherein the pressure generator produces an oscillating pneumatic pressure waveform in the garment, wherein the oscillating pneumatic pressure waveform is created by a plurality of independently controlled sinusoidal pneumatic generators, wherein each of the plurality of straps is connected to a respective one of the plurality of independently controlled sinusoidal pneumatic generators.

2. The high frequency chest wall oscillator of claim 1 wherein each of the plurality of sinusoidal pneumatic generators is controlled to set the shape, frequency, and amplitude of the oscillating pneumatic pressure waveform.

3. The high frequency chest wall oscillator of claim 1 wherein each of the plurality of straps are cyclically retracted and expanded to oscillate the volume of pressurized air in the inflatable chamber.

4. The high frequency chest wall oscillator of claim 3 wherein the oscillating pneumatic pressure waveform has a frequency in the range of 5 to 25 Hz.

5. The high frequency chest wall oscillator of claim 3 wherein the pressurized air is between 0.0 and 6.9 kPa.

6. The high frequency chest wall oscillator of claim 5 further comprising:
   a power source for providing electrical power to the pressure generator.

7. The high frequency chest wall oscillator of claim 6 wherein the pressure generator requires less than 100 Watts of electrical power.

8. The high frequency chest wall oscillator of claim 7 wherein the power source is a battery array.

9. The high frequency chest wall oscillator of claim 8 wherein the power source, garment, pressure generator, blower, and plurality of straps are all positionable on the torso of the user.

10. A high frequency chest wall oscillator wearable about the chest of a user of the type having an inflatable vest with retractable bands attached thereto comprising:
   a plurality of independently controlled sinusoidal pneumatic pressure generators, wherein each of the retractable bands is connected to a respective one of the plurality of independently controlled sinusoidal pressure generators, wherein the output amplitude of each of the plurality of independently controlled pressure generators is limited to prevent harm to a user;
   and wherein each of the plurality of independently controlled sinusoidal pneumatic pressure generators produce an oscillating pressure waveform within the vest.

11. The high frequency chest wall oscillator of claim 10 further comprising:
   a pneumatic pressure sensor in communication with a microcontroller; wherein the microcontroller continuously monitors the oscillating pressure waveform.

12. The high frequency chest wall oscillator of claim 11 wherein the microcontroller communicates a warning if the oscillating pressure waveform falls outside preset limits.

13. The high frequency chest wall oscillator of claim 11 wherein the microcontroller compares the oscillating pressure waveform with prescribed settings.

14. The high frequency chest wall oscillator of claim 11 wherein the microcontroller monitors and records parameters associated with a therapy session.

15. The high frequency chest wall oscillator of claim 14 wherein the microcontroller compares the parameters with a heart rate and breathing cycle of a user.

16. The high frequency chest wall oscillator of claim 11 further comprising:
   an electrical system including a battery array attached to the plurality of sinusoidal pneumatic pressure generators.

17. The high frequency chest wall oscillator of claim 16 wherein the electrical system includes failsafe shock circuitry and fire protection circuitry.

* * * * *